(12) United States Patent
Nagy et al.

(10) Patent No.: US 11,980,872 B2
(45) Date of Patent: May 14, 2024

(54) EPOXIDATION PROCESSES AND CATALYSTS FOR USE THEREIN

(71) Applicant: Lyondell Chemical Technology, L.P., Houston, TX (US)

(72) Inventors: Sandor Nagy, Seabrook, TX (US); Barbara Kimmich, Houston, TX (US)

(73) Assignee: Lyondell Chemical Technology, L.P., Houston, TX (US)

( * ) Notice: Subject to any disclaimer, the term of this patent is extended or adjusted under 35 U.S.C. 154(b) by 971 days.

(21) Appl. No.: 16/931,677

(22) Filed: Jul. 17, 2020

(65) Prior Publication Data

US 2020/0346193 A1     Nov. 5, 2020

Related U.S. Application Data

(62) Division of application No. 15/244,936, filed on Aug. 23, 2016, now abandoned.

(60) Provisional application No. 62/363,401, filed on Jul. 18, 2016, provisional application No. 62/211,117, filed on Aug. 28, 2015.

(51) Int. Cl.

| | |
|---|---|
| *B01J 23/66* | (2006.01) |
| *B01J 21/16* | (2006.01) |
| *B01J 23/50* | (2006.01) |
| *B01J 23/68* | (2006.01) |
| *B01J 23/89* | (2006.01) |
| *B01J 31/26* | (2006.01) |
| *B01J 35/00* | (2006.01) |
| *B01J 37/02* | (2006.01) |
| *B01J 37/08* | (2006.01) |
| *C07D 301/03* | (2006.01) |
| *C07D 301/10* | (2006.01) |

(52) U.S. Cl.
CPC ............... *B01J 23/66* (2013.01); *B01J 21/16* (2013.01); *B01J 23/50* (2013.01); *B01J 23/688* (2013.01); *B01J 35/19* (2024.01); *B01J 37/0203* (2013.01); *B01J 37/0205* (2013.01); *B01J 37/0215* (2013.01); *B01J 37/0236* (2013.01); *B01J 37/088* (2013.01); *C07D 301/03* (2013.01); *C07D 301/10* (2013.01); *B01J 23/687* (2013.01); *B01J 23/89* (2013.01); *B01J 31/26* (2013.01); *B01J 37/0213* (2013.01)

(58) Field of Classification Search
None
See application file for complete search history.

(56) References Cited

U.S. PATENT DOCUMENTS

| | | | |
|---|---|---|---|
| 3,431,218 A | 3/1969 | Plank et al. | |
| 4,123,385 A | 10/1978 | Rebsdat et al. | |
| 4,255,341 A | 3/1981 | Solomon | |
| 2005/0245701 A1 | 11/2005 | Oshima et al. | |
| 2007/0111886 A1 | 5/2007 | Serafin et al. | |
| 2010/0261005 A1 | 10/2010 | Santaren Rome et al. | |
| 2012/0264953 A1 | 10/2012 | Rosendahl et al. | |

FOREIGN PATENT DOCUMENTS

| | | |
|---|---|---|
| CN | 1297443 A | 5/2001 |
| CN | 1330644 A | 1/2002 |
| CN | 101184740 A | 5/2008 |
| CN | 101193702 A | 6/2008 |
| CN | 101767039 A | 7/2010 |
| CN | 101965224 A | 2/2011 |
| CN | 102133544 A | 7/2011 |
| CN | 102139212 A | 8/2011 |
| CN | 102527430 A | 7/2012 |
| CN | 104066504 A | 9/2014 |
| CN | 104275211 A | 1/2015 |
| CN | 104549544 A | 4/2015 |
| CN | 104707592 A | 6/2015 |

OTHER PUBLICATIONS

Adams et al, Journal of Physical Science, vol. 24, No. 1, pp. 61-74 (Year: 2013).*
The International Search Report and Written Opinion for PCT/US2016/048215 dated Jan. 4, 2017.
Practical Handbook of Nobel Metal Production Technology, Metallurgical Industry Press, Edition 1, p. 79, Jan. 2011, ISBN 978-7-5024-5373-2, Beijing, China.

\* cited by examiner

*Primary Examiner* — Zinna Northington Davis

(57) ABSTRACT

Epoxidation methods and catalyst are described herein. The epoxidation catalysts generally include a metal component including silver and a support material including kaolinite, wherein the epoxidation catalyst includes less than 55 wt. % metal component.

16 Claims, No Drawings

EPOXIDATION PROCESSES AND CATALYSTS FOR USE THEREIN

CROSS-REFERENCE TO RELATED APPLICATIONS

This application is a divisional patent application of U.S. patent application Ser. No. 15/244,936, filed on Aug. 23, 2016, which claims the benefit of priority to U.S. Provisional Application No. 62/211,117 filed on Aug. 28, 2015, and U.S. Provisional Application No. 62/363,401 filed Jul. 18, 2016, both of which are incorporated herein by reference in their entirety.

STATEMENT REGARDING FEDERALLY SPONSORED RESEARCH OR DEVELOPMENT

Not applicable.

FIELD

Embodiments as described herein generally relate to epoxidation catalyst compositions and methods of making and using the same.

BACKGROUND

This section introduces information from the art that may be related to or provide context for some aspects of the techniques described herein and/or claimed below. This information is background facilitating a better understanding of that which is disclosed herein. Such background may include a discussion of "related" art. That such art is related in no way implies that it is also "prior" art. The related art may or may not be prior art. The discussion is to be read in this light, and not as admissions of prior art.

Catalytic epoxidation of olefins with oxygen is an industrially important process for preparing compounds such as ethylene oxide and propylene oxide, for example. Traditionally, epoxidation catalyst compositions generally include a solid support, such as a calcium carbonate support. However, conventional supports can be difficult to shape and process. Furthermore, efforts are continuously underway to improve the productivity and selectivity of epoxidation catalysts.

Contained herein are embodiments directed to resolving, or at least reducing, one or all of the problems mentioned above.

SUMMARY

Embodiments as described herein include epoxidation catalyst compositions. The catalyst generally includes silver having an oxidation state of zero; and a phyllosilicate solid component; wherein the silver is deposited on the phyllosilicate solid component.

One or more embodiments include the catalyst of the preceding paragraph, wherein the phyllosilicate solid component is a clay mineral group phyllosilicate.

One or more embodiments include the catalyst of any preceding paragraph, wherein the phyllosilicate solid component is talc, kaolinite, or pyrophillite.

One or more embodiments include the catalyst of any preceding paragraph, wherein the catalyst further includes a Group 1 metal salt.

One or more embodiments include the catalyst of the preceding paragraph, wherein the Group 1 metal salt is $KNO_3$.

One or more embodiments include the catalyst of any preceding paragraph, wherein the catalyst further includes a promoter metal selected from: rhenium, tungsten, zinc, nickel, gold, copper, sodium, potassium, lithium, rubidium, cesium, or molybdenum.

One or more embodiments include the catalyst of any preceding paragraph, wherein the promoter metal is rhenium.

One or more embodiments include the catalyst of any preceding paragraph, wherein the catalyst includes from about 10 wt. % to about 70 wt. % of silver.

One or more embodiments include the catalyst of any preceding paragraph, wherein the catalyst includes from about 0.05 wt. % to about 10 wt. % of the Group 1 metal nitrate salt.

One or more embodiments include the catalyst of any preceding paragraph, wherein the catalyst includes from about 0.0 wt. % to about 5.0 wt. % of the promoter metal.

One or more embodiments include epoxidation methods including obtaining a phyllosilicate solid component; and depositing silver having an oxidation state of zero on the phyllosilicate solid component to form a silver catalyst.

One or more embodiments include the method of the preceding paragraph, and further including calcinating the silver catalyst at a temperature from about 250° C. to about 800° C. to form a calcinated silver catalyst.

One or more embodiments include the method of the preceding paragraph, wherein the temperature is from about 250° C. to about 600° C.

One or more embodiments include the catalyst of any preceding paragraph, further including depositing a promoter metal onto the silver catalyst to form a promoter deposited silver catalyst.

One or more embodiments include the catalyst of any preceding paragraph, further including depositing a Group 1 nitrate salt onto the silver catalyst to form a Group 1 nitrate deposited silver catalyst.

One or more embodiments include the catalyst of any preceding paragraph, wherein the silver catalyst comprises from about 10 wt. % to about 70 wt. % silver.

One or more embodiments include the catalyst of any preceding paragraph, wherein the promoter deposited silver catalyst includes from about 0.0 wt. % to about 5.0 wt. % promoter metal deposited on the silver catalyst.

One or more embodiments include the catalyst of any preceding paragraph, wherein the Group 1 metal nitrate deposited silver catalyst includes from about 1.0 wt. % to about 8.0 wt. % of the Group 1 metal nitrate deposited on the silver catalyst.

One or more embodiments include the catalyst of any preceding paragraph, further including drying the calcinated silver catalyst at a temperature from about 100° C. to about 200° C. to form a dried calcinated silver catalyst.

One or more embodiments include a method including obtaining the catalyst of any preceding claim; and contacting the catalyst with molecular oxygen and an α-olefin($C_{2-12}$) to form an epoxide($C_{2-12}$).

One or more embodiments include an epoxidation catalyst including a metal component including silver and a support material including kaolinite, wherein the epoxidation catalyst includes less than 55 wt. % metal component.

One or more embodiments include the catalyst of the preceding paragraph, further including a Group 1 metal salt.

One or more embodiments include the catalyst of the preceding paragraph and further including a promoter metal selected from rhenium, tungsten, zinc, nickel, gold, copper, sodium, potassium, lithium, rubidium, cesium, molybdenum or combinations thereof.

One or more embodiments include a method of forming an epoxide including contacting an olefin with an oxidizing agent in the presence of the catalyst of any preceding paragraph to form the epoxide.

One or more embodiments include the method of the preceding paragraph, wherein the olefin includes propylene and the epoxide includes propylene epoxide.

One or more embodiments include the method of forming the epoxide of any preceding paragraph exhibiting a conversion that is increased by at least 10% over an identical process but with a metal content greater than 55 wt. %.

One or more embodiments include the method of forming the epoxide of any preceding paragraph exhibiting a selectivity that is increased by at least 5% over an identical process but with a metal content greater than the 55 wt. %.

While multiple embodiments are disclosed, still other embodiments will become apparent to those skilled in the art from the following detailed description. As will be apparent, certain embodiments, as disclosed herein, are capable of modifications in various obvious aspects, all without departing from the spirit and scope of the claims as presented herein. Accordingly, the drawings and detailed description are to be regarded as illustrative in nature and not restrictive.

DETAILED DESCRIPTION

Illustrative embodiments of the subject matter claimed below will now be disclosed. In the interest of clarity, not all features of an actual implementation are described in this specification. It will be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort, even if complex and time-consuming, would be a routine undertaking for those of ordinary skill in the art having the benefit of this disclosure.

The embodiments illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. Further, various ranges and/or numerical limitations may be expressly stated below. It should be recognized that unless stated otherwise, it is intended that endpoints are to be interchangeable. Further, any ranges include iterative ranges of like magnitude falling within the expressly stated ranges or limitations disclosed herein is to be understood to set forth every number and range encompassed within the broader range of values. It is to be noted that the terms "range" and "ranging" as used herein generally refer to a value within a specified range and encompasses all values within that entire specified range.

As used herein, the terms "up" and "down", "upper" and "lower", "upwardly" and "downwardly", "upstream" and "downstream", "above" and "below" and other like terms indicating relative positions above or below a given point or element are used in this description to more clearly describe some embodiments. However, when applied to equipment and methods for use in wells that are deviated or horizontal, such terms may refer to a left to right, right to left or other relationship as appropriate.

Furthermore, various modifications may be made within the scope of the embodiments as herein intended, and embodiments as described herein may include combinations of features other than those expressly claimed. In particular, flow arrangements other than those expressly described herein are within the scope of the embodiments.

Various terms as used herein are shown below. To the extent a term used in a claim is not defined below, it should be given the broadest definition skilled persons in the pertinent art have given that term as reflected in printed publications and issued patents at the time of filing. Further, unless otherwise specified, all compounds described herein may be substituted or unsubstituted and the listing of compounds includes derivatives thereof.

Further, various ranges and/or numerical limitations may be expressly stated below. It should be recognized that unless stated otherwise, it is intended that endpoints are to be interchangeable. Further, any ranges include iterative ranges of like magnitude falling within the expressly stated ranges or limitations.

For the groups and classes below, the number of carbon atoms in the group is as indicated as follows: "Cn" defines the exact number (n) of carbon atoms in the group/class. "C≤n" defines the maximum number (n) of carbon atoms that can be in the group/class, with the minimum number as small as possible for the group in question, e.g., it is understood that the minimum number of carbon atoms in the group "alkenyl(C≤8)" or the class "alkene(C≤8)" is two.

The term "saturated" when used to modify a compound or an atom means the compound or atom has no carbon-carbon double and no carbon-carbon triple bonds, except as noted below. When the term "saturated" is used in the context of a solution and a solute, it means that no more of that substance can be dissolved in that solution.

The term "aliphatic" when used without the "substituted" modifier signifies that the compound/group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single carbon-carbon bonds (alkanes/alkyl), or unsaturated, with one or more carbon-carbon double bonds (alkenes/alkenyl) or with one or more carbon-carbon triple bonds (alkynes/alkynyl).

The term "alkyl" refers to a monovalent saturated aliphatic group with a carbon atom as the point of attachment, a linear or branched acyclic structure, and no atoms other than carbon and hydrogen. An "alkane" refers to the class of compounds having the formula H—R, wherein R is alkyl as this term is defined above.

The term "alkenyl" refers to a monovalent unsaturated aliphatic group with a carbon atom as the point of attachment, a linear or branched, acyclic structure, at least one nonaromatic carbon-carbon double bond, no carbon-carbon triple bonds, and no atoms other than carbon and hydrogen. The terms "alkene" or "olefin" are synonymous and refer to the class of compounds having the formula H—R, wherein R is alkenyl as this term is defined above. A "terminal alkene" refers to an alkene having just one carbon-carbon double bond, wherein that bond forms a vinyl group at one end of the molecule.

The term "aryl" refers to a monovalent unsaturated aromatic group with an aromatic carbon atom as the point of attachment, said carbon atom forming part of a one or more six-membered aromatic ring structure, wherein the ring atoms are all carbon, and wherein the group consists of no atoms other than carbon and hydrogen. If more than one ring is present, the rings may be fused or unfused. As used herein, the term does not preclude the presence of one or more alkyl or aralkyl groups (carbon number limitation permitting) attached to the first aromatic ring or any additional aromatic ring present. An "arene" refers to the class of compounds having the formula H—R, wherein R is aryl as that term is defined above. Benzene and toluene are non-limiting examples of arenes.

The term "arylalkene" when used without the "substituted" modifier refers to the class of compounds having the formula aryl-alkenyl, in which the terms aryl and alkenyl are each used in a manner consistent with the definitions provided above.

The term "epoxide" refers to a class of compounds of the formula:

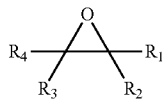

wherein $R_1$, $R_2$, and $R_3$ are each independently hydrogen, alkyl, and $R_4$ is hydrogen, alkyl, or aryl.

The term "Florisil®" represents a magnesium silicate with CAS Registry Number 1343-88-0.

The term "Group 1 metal" represents metal atom(s) selected from lithium, sodium, potassium, rubidium, and cesium. The term "Group 2 metal" represents metal atom(s) selected from beryllium, magnesium, calcium, strontium, and barium. The term "transition metal" represents metal atom(s) selected from the elements from scandium through zinc, yttrium through cadmium, and lutetium through mercury on the periodic table. The term "lanthanoid" represents metal atom(s) selected from the elements from lanthanide through ytterbium on the periodic table.

Epoxidation catalyst compositions and methods of epoxidation of olefins are described herein. Epoxidation of olefins generally includes contacting an olefin with an oxidizing agent in the presence of an epoxidation catalyst composition to form an epoxide.

The epoxidation catalyst compositions generally include a support material and a metal component.

The metal component is generally a noble metal, such as palladium, gold, platinum, silver, iridium, ruthenium, osmium or combinations thereof, for example. In one or more embodiments, the noble metal is silver. In one or more embodiments, the silver which is present within the epoxidation catalyst composition in the zero oxidation state (e.g., elemental silver). Alternatively, or in combination therewith, the silver is present in a cationic oxidation state. When present in both the zero oxidation state and the cationic oxidation state, one or more embodiments include more silver in the zero oxidation state that in the cationic oxidation state. It is further contemplated that the silver may be deposited on the support material as cationic silver and then may be reduced to elemental silver.

The support material generally includes a phyllosilicate solid component (i.e., phyllosilicate), which may be synonymously referred to herein as "phyllosilicate", "crystalline phyllosilicate", and "layered silicate". A wide variety of different phyllosilicates may be utilized as the support material. Phyllosilicates are generally layered silicates which can be characterized as platy or micaceous and are soft, flexible and elastic relative to other minerals. Phyllosilicates generally include sheets of tetrahedral formed by oxygen atoms around silicon atoms with alternating sheets of either octahedral or other polyhedral with higher coordination numbers formed by divalent or trivalent cations and oxygen atoms of the silicate and hydroxide groups. The tetrahedral layer generally includes silica oxide where the vertex of the tetrahedral contains three oxygen atoms shared with other tetrahedral forming interconnected six member rings extending outward. The octahedral or other polyhedral are formed by the divalent and trivalent cations chelated with the apical oxygen atoms and the hydroxide which may be present in the center of the six member rings formed by the tetrahedral layer of the silica oxide. Phyllosilicates as disclosed herein are generally crystalline in the sense that the phyllosilicate has an ordered structure providing an x-ray diffraction pattern with distinct maxima.

The octahedral or polyhedral layer generally includes two major classifications: a brucite type structure including divalent cations with octahedral binding sites occupied with hydroxides and gibbsite type structure which include trivalent cations with every third cation site being unoccupied and the binding sites are occupied by hydroxides. These major classifications of the octahedral layer give rise to two major classes: dioctahedral and trioctahedral. For dioctahedral group phyllosilicates, the octahedral sheet contains trivalent cations such as aluminum cations. Within the dioctahedral group, the group has two structural types, t-o and t-o-t. The t-o structural type contains alternating layers of tetrahedral and octahedral sheets and is also known as a 1:1 dicotahedral group phyllosilciate. The t-o-t structural type contains alternating groups of a tetrahedral sheet, an octahedral sheet, and a tetrahedral sheet. The trioctahedral group phyllosilicate have octahedral sheets contains divalent cations such as iron or magnesium. Similar to the dioctahedral group phyllosilicates, a trioctahedral phyllosilicate may have either a t-o-t structural type or a t-o structural type as described above.

The phyllosilicates are generally divided into four groups of phyllosilicates: serpentine, clay mineral, mica, or chlorite groups. The serpentine group of phyllosilicates have the chemical formula: $Mg_3Si_2O_5(OH)_4$ such as antigorite, chrysotile, and lizardite, for example. These serpentine group of phyllosilicates generally exhibit monoclinic crystalline symmetry but may also exhibit either orthorhombic or hexagonal crystalline symmetry, for example. The mica group of phyllosilicates includes compounds with strong birefringence, have nearly perfect basal cleavage, and have monoclinic crystalline symmetry. These compounds have the general chemical formula: $X_2Y_4\text{-}6Z_8O_{20}(OH,F)_4$ wherein X is K, Na, Ca, or other Group 1 or Group 2 metals, Y is Al, Mg, or Fe, and Z is either Si or A but may also be $Fe^{3+}$ or Ti. Mica group phyllosilicates can be either dioctahedral or trioctahedral. Some non-limiting examples of mica group phyllosilicates include biotite, muscovite, phlogopite, lepidolite, margarite, phengite, hydro-muscovite, phologpite, zinnwaldite, and glauconite, for example. The chlorite group of phyllosilicates includes compounds which have the general formula: $(Mg,Fe)_3(Si,Al)_4O_{10}(OH)_2 \cdot (Mg,Fe)_3(OH)_6$ wherein one or more elements such as Mg, Fe, Ni, Mn, Li, Ca, or Zn have been substituted into the silicate lattice and have a t-o-t structure wherein the $(Mg, Fe)(OH)_6$ unit is spaced between each of the t-o-t repeats. These compounds are monoclinic but some also have triclinic polymorphs. Some non-limiting examples of chlorite phyllosilicates include baileychlore, chamosite, clinochlore, cookeite, donbassite, gonyerite, nimite, odinite, orthochamosite, pennantite, ripidolite, or sudoite, for example.

In one or more embodiments, the phyllosilicate is a clay mineral phyllosilicate. Clay mineral phyllosilicates are hydrous aluminum phyllosilicates with contain variable amounts of iron, magnesium, Group 1 metals, Group 2 metals, or other cations. The clay mineral phyllosilicates contain octahedral hydroxide sheets and tetrahedral silicate or alumina sheets which may be in either 1:1 tetrahedral to octahedral sheets or 2:1 tetrahedral to octahedral sheets. In these clay mineral phyllosilicates, the octahedral and tetrahedral sheets are linked by small cationic ions such as Mg or Al with the unshared oxygen atom of the silicate or alumina sheet pointing in the same direction (e.g., on the same side of the sheet). In order to adopt the appropriate bonding pattern, the tetrahedral sheet may become twisted or corrugated while the octahedral sheet is flattened. Clay mineral phyllosilicates may adopt a variety of crystal forms including but not limited to monoclinic and triclinic. Some non-limiting examples of clay mineral phyllosilicates include halloysite, kaolinite, illite, montmorillonite, vermiculite, talc, sepiolite, palygorskite, and pyrophyllite, for example.

In one or more embodiments, the phyllosilicate is a clay mineral phyllosilicate such as talc, kaolinite, or pyrophyllite. In some embodiments, the phyllosilicate solid component is talc. Talc is a trioctahedral phyllosilicate with a t-o-t structure and no net charge on either sheet with a formula of $Mg_3Si_4O_{10}(OH)_2$. Talc has either a monoclinic or triclinic crystal symmetry.

In one or more embodiments, the phyllosilicate is kaolinite. Kaolinite is a dioctahedral phyllosilicate with a t-o structure, pH dependent charge, no interlayer cations, and a formula of $Al_2Si_2O_5(OH)_4$. Kaolinite is a part of a broader group of minerals known as kaolins which includes dickite, nacrite, halloysite, and kaolinite. Additionally, kaolinite has a triclinic crystal symmetry. In other embodiments, the phyllosilicate solid component is pyrophyllite. Pyrophyllite is a dioctahedral phyllosilicate with a t-o-t structure, no net charge, and a formula of $Al_2Si_4O_{10}(OH)_2$. Pyrophyllite has either a monoclinic or triclinic crystal symmetry.

The metal component may be incorporated into the catalyst by supporting the metal component on the support material to form the epoxidation catalyst composition. A wide variety of sources may be utilized to deposit the metal component onto the support material, such as metal salts. Some non-limiting examples of salts may include oxalates, acetates, citrates, malonates, complexing agents, stabilizing agents and combinations thereof, for example. Additional sources of metal components include those described in U.S. Pat. No. 5,861,519, which is incorporated by reference in its entirety herein. In one or more embodiments, the source of the metal component includes metal oxides. In other embodiments, the source is a metal carboxylate. In yet other embodiments, the source includes a metal oxide with one or more stabilizing or complexing agents. For example, the stabilizing or complexing agent is a fatty acid or an amine containing alkyl group, such as ethylenediamine or ethanolamine.

The epoxidation catalyst composition generally includes the metal component in an amount in a range of 5 wt. % to 80 wt. %, or 10 wt. % to 70 wt. %, or 40 wt. % to 60 wt. %, based on the total amount of epoxidation catalyst composition, for example. However, in one or more embodiments, the epoxidation catalyst composition includes a reduced loading of metal component. For example, in one or more embodiments, the epoxidation catalyst composition includes the metal component in an amount in a range of 5 wt. % to 50 wt. %, or 10 wt. % to 48 wt. %, or 40 wt. % to 47 wt. %, or less than 55 wt. %, based on the total amount of epoxidation catalyst composition, for example. At such reduced metal loading, conversion, selectivity and productivity are unexpectedly increased. For example, the reduced metal loading concentrations may result in a conversion that is increased by at least 5%, or at least 10%, or at least 15% or at least 20%, over an identical process but with a metal content greater than the reduced content described herein. The reduced metal loading concentrations may result in a selectivity that is increased by at least 2%, or at least 5%, or at least 7% or at least 8%, over an identical process but with a metal content greater than the reduced content described herein.

The epoxidation catalyst composition may further include a Group 1 metal salt. Non-limiting examples of Group 1 metal salts include Group 1 metal nitrate salts, for example. For example, the Group 1 metal nitrate salt may include lithium nitrate, sodium nitrate, potassium nitrate or combinations thereof. When present in the epoxidation catalyst composition, the epoxidation catalyst composition may include the Group 1 metal salt in an amount in a range of 0.01 wt. % to 10 wt. %, or 0.5 wt. % to 8 wt. %, or 1 wt. % to 6 wt. % based on the total weight of epoxidation catalyst.

The epoxidation catalyst composition may further include an additional promoter or activator metal. In some embodiments, the additional promoter or activator metal is deposited on the support material concurrently with the metal component. In other embodiments, the additional promoter or activator metal is deposited on the support material after the deposition of the metal component.

The additional promoter may include a promoter metal, such as rhenium, molybdenum, tungsten, iron, nickel, copper, zinc, scandium, ytterbium, other lanthanoid metals or combinations thereof. In one or more embodiments, the promoter metal is rhenium. In some embodiments, a commercially available salt of these metals may be used to prepare the epoxidation catalyst composition including such promoter metals. When present in the epoxidation catalyst composition, the epoxidation catalyst composition may include the additional promoter in an amount in a range of 0.01 wt. % to 5 wt. %, or 0.5 wt. % to 2 wt. %, or 0.1 wt. % to 1 wt. % based on the total weight of epoxidation catalyst.

One or more components of the epoxidation catalyst composition may be calcined at an elevated temperature in the presence of air. The calcining temperature may be in a range of 150° C. to 800° C., or 200° C. to 400° C., or 250° C. to 350° C., for example.

As indicated elsewhere herein, the epoxidation catalyst compositions are used to form epoxides. Once the epoxidation catalyst composition is prepared, as described above and/or as known to one skilled in the art, a variety of processes may be carried out using that composition. The equipment, process conditions, reactants, additives and other materials used in polymerization processes will vary in a given process, depending on the desired composition and properties of the epoxide to be formed. Such processes may include vapor phase processes, gas phase processes or combinations thereof, for example. (See, U.S. Pat. Nos. 5,525,741, 5,703,254 and 5,856,534, U.S. Patent Publ. No. 2005/0027134, U.S. Patent Publ. No. 2012/0277446, PCT Publication WO 2004/039496 and PCT Publication WO 2011/074508, which are incorporated by reference in their entirety herein.)

In certain embodiments, the processes described above generally include epoxidation of one or more olefins in the presence of an oxidizing agent to form epoxides. The olefins may include ethylene, propylene, 1-butene, 1-pentene, 1-hexene, 1-octene, styrene or combinations thereof, for example. In one or more specific embodiments, the olefin includes propylene and the epoxide is propylene oxide.

In one or more embodiments, the oxidizing agent includes molecular oxygen ($O_2$). In one or more embodiments, the molecular oxygen is generated from an oxygen source, such as air or a compound which generates molecular oxygen in situ. The compound which generates molecular oxygen is a gas under epoxidation conditions. For example, the oxygen source may be an atmospheric gas (e.g., air).

In one or more embodiments, the olefin is introduced into the epoxidation reaction in an amount in a range of 0.1 vol. % to 50 vol. %, or 1 vol. % to 20 vol. %, or 2 vol. % to 10 vol. % based on the total volume of reaction mixture. In one or more embodiments, the oxidizing agent is introduced into the epoxidation reaction in an amount in a range of 1 vol. % to 11 vol. %, or 2 vol. % to 10 vol. %, or 4 vol. % to 9 vol. % based on the total volume of reaction mixture. In one or more embodiments, the olefin and the epoxidation catalyst composition are introduced to the input stream prior to the introduction of oxidizing agent. In one or more embodiments, the buildup of excess oxygen in the process is prevented by pulsing the introduction of the oxidizing agent.

In one or more embodiments, the olefin contacts the oxidizing agent at an epoxidation temperature in a range of 100° C. to 500° C., or 150° C. to 400° C., or 200° C. to 300° C., for example. The olefin may contact the oxidizing agent at an epoxidation pressure in a range of 1 barg to 30 barg, or 1 barg to 10 barg, or 2 barg to 4 barg, for example.

In one or more embodiments, the olefin contacts the oxidizing agent for a contact time sufficient to provide a gas hourly space velocity (GHSV) in a range of 100 $hr^{-1}$ to 10,000 $hr^{-1}$, or 200 $hr^{-1}$ to 5,000 $hr^{-1}$, or 500 $hr^{-1}$ to 2,000 $hr^{-1}$, for example.

In one or more embodiments, the epoxidation process exhibits a conversion in a range of 0.5% to 90%. For example, one or more embodiments may exhibit a conversion percentage of greater than 4.5% of the olefin. The term "conversion" refers to the percentage of input converted. As used herein, "conversion" can be used to evaluate the activity or efficiency of the catalyst composition and is generally calculated via the following equation: conversion (%)=epoxide (wt.)/olefin fed (wt.)*100.

The epoxidation process may further include the introduction of one or more additives to the reaction mixture, the olefin, the epoxide or combinations thereof. Non-limiting examples of additives include water, carbon dioxide, nitrogen containing compounds, $NO_x$ gases (e.g., NO and $NO_2$), organic halides, CO, $PH_3$, $SO_2$, $SO_3$ and combinations thereof. The nitrogen-containing compounds may include hydrazine, ammonia, methyl amine or combinations thereof, for example. In one or more specific embodiments, the one or more additives include $CO_2$. In one or more embodiments, the one or more additives are introduced into the epoxidation reaction in an amount in a range of 10 ppm to 500 ppm, or 30 ppm to 300 ppm, or 50 ppm to 200 ppm, based on the total weight of reaction mixture, for example. In one or more embodiments utilizing $CO_2$ as an additive, the reaction mixture may include $CO_2$ in a range of 0.01 vol. % to 50 vol. %, or 0.1 vol. % to 20 vol. %, or 1 vol. % to 10 vol. % based on the total volume of reaction mixture, for example. In alternative embodiments, the one or more additives are absent $CO_2$. The use and inclusion of $CO_2$ in epoxidation processes is described, for example, in U.S. Pat. No. 5,625,084, which is incorporated by reference in its entirety herein.

The epoxidation process may further include the introduction of one or more organic halides to the reaction mixture, the olefin, the epoxide or combinations thereof. In some embodiments, the organic halide is a gas at room temperature or the organic halide is gaseous at the epoxidation temperature and epoxidation pressure. Non-limiting examples of the organic halide include ethylene dichloride, ethyl chloride, vinyl chloride, methyl chloride, and methylene chloride, for example. In some embodiments, organic halides which may be used in the epoxidation methods provided herein include those described in Japanese Publication No. 2008184456A, which is incorporated by reference in its entirety herein. In some embodiments, the organic halide is a gas below 100° C. and at atmosphere pressure. In one or more embodiments, the one or more organic halides are introduced into the epoxidation reaction in an amount in a range of 10 ppm to 500 ppm, or 50 ppm to 400 ppm, or 100 ppm to 300 ppm, based on the total weight of reaction mixture, for example.

The epoxidation process may further include the utilization of unreactive gas molecules as a diluent, a carrier, an inert reaction medium or combinations thereof. Such gas molecules may be referred to as ballast gas. Non-limiting examples of ballast gas include hydrocarbons, noble gases, CO, $CO_2$, $N_2$ and combinations thereof. In one or more specific embodiments, the ballast gas includes $N_2$.

The above methods can be further modified and optimized for preparative, pilot- or large-scale production, either batch or continuous, using the principles and techniques of process chemistry as applied by a person skilled in the art. Such principles and techniques are taught, for example, in *Practical Process Research & Development* (2012).

EXAMPLES

To facilitate a better understanding of the disclosure, the following examples of embodiments are given. In no way should the following examples be read to limit, or to define, the scope of the appended claims.

Example 1

Catalyst Preparation for the Catalyst of Table 1

A. Run 1: To 11.0 mL of deionized water 11.06 g of ethylenediamine was added followed by slow addition of 11.02 g oxalic acid dihydrate at 50° C. To the resulting homogeneous solution 20.63 g of silver oxide and 4.0 g of ethanolamine at 50° C. and stirred until dissolved. The resulting solution was combined with 14 g of scalenohedral $CaCO_3$ (Vicality Light Grade from Specialty Minerals Co.) and mixed well into a homogeneous thick paste, which was placed in an oven at 110° C. for 1 hour then heated to 300° C. at the rate of 20° C. per minute and calcined at this temperature for 4 hours. A 16.90 g sample of the calcined material was suspended in a solution of 0.851 g of $KNO_3$ in 38 mL of deionized water stirred for 30 minutes and rotovaped dry at 60° C. followed by calcination for 2 hours at 110° C. The nominal composition of the catalyst: 55.1 wt. % Ag and 4.8 wt. % $KNO_3$.

B. Run 2: To 11.0 mL of deionized water 11.04 g of ethylenediamine was added followed by slow addition of 11.12 g oxalic acid dihydrate at 50° C. To the resulting homogeneous solution 20.32 g of silver oxide and 4.0 g of ethanolamine at 50° C. and stirred until dissolved, followed by addition of 0.537 g of $(NH_4)_6Mo_7O_{24}$ tetrahydrate. The resulting solution was combined with 14.06 g of scalenohedral $CaCO_3$ (Vicality Light Grade from Specialty Minerals Co.) and mixed well into a homogeneous thick paste, which was placed in an oven at 110° C. for 1 hour then heated to 300° C. at the rate of 20° C. per minute and calcined at this temperature for 4 hours. A 27.81 g sample of the calcined material was suspended in a solution of 1.69 g of $KNO_3$ in 63 mL of deionized water stirred for 30 minutes and rotovaped dry at 60° C. followed by calcination for 2 hours at 110° C. The nominal composition of the catalyst: 53.7 wt. % Ag, 0.92 wt. % Mo and 5.7 wt. % $KNO_3$.

C. Run 3: To 8.46 mL of deionized water 8.48 g of ethylenediamine was added followed by slow addition of 8.48 g oxalic acid dihydrate at 50° C. To the resulting homogeneous solution 14.46 g of silver oxide and 3.0 g of ethanolamine at 50° C. and stirred until dissolved. To a half portion of the resulting solution 0.104 g of $NH_4ReO_4$ was added and the resulting solution was combined with 6.22 g of scalenohedral $CaCO_3$ (Vicality Light Grade from Specialty Minerals Co.) and mixed well into a homogeneous thick paste, which was placed in an oven at 110° C. for 1 hour then heated to 300° C. at the rate of 20° C. per minute and calcined at this temperature for 4 hours. A 4.02 g sample of the calcined material was suspended in a solution of 0.197 g of $KNO_3$ in 9 mL of deionized water stirred for 30 minutes and rotovaped dry at 60° C. followed by calcination for 2 hours at 110° C. The nominal composition of the catalyst: 49.2 wt. % Ag, 0.55 wt. % Re and 4.7 wt. % $KNO_3$.

D. Run 4: To 11.25 mL of deionized water 11.01 g of ethylenediamine was added followed by slow addition of 11.0 g oxalic acid dihydrate at 50° C. To the resulting homogeneous solution 20.23 g of silver oxide and 4.0 g of ethanolamine at 50° C. and stirred until dissolved. ⅓ portion of the resulting solution was combined with 4.7 g of $Ca(OH)_2$ (Sigma Aldrich) and mixed well into a homogeneous thick paste, which was placed in an oven at 110° C. for 1 hour then heated to 300° C. at the rate of 20° C. per minute and calcined at this temperature for 4 hours. A 4.02 g sample of the calcined material was suspended in a solution of 0.197 g of $KNO_3$ in 17 mL of deionized water stirred for 30 minutes and rotovaped dry at 60° C. followed by calcination for 2 hours at 110° C. The nominal composition of the catalyst: 54.2 wt. % Ag and 5.7 wt. % $KNO_3$.

E. Run 5: To 11.03 mL of deionized water 11.05 g of ethylenediamine was added followed by slow addition of 11.08 g oxalic acid dihydrate at 50° C. To the resulting homogeneous solution 20.30 g of silver oxide and 4.0 g of ethanolamine at 50° C. and stirred until dissolved. ⅓ portion of the resulting solution was combined with 4.7 g of alpha-$Al_2O_3$ (Norpro, sieved 20 mesh) and mixed well into a homogeneous thick paste, which was placed in an oven at 110° C. for 1 hour then heated to 300° C. at the rate of 20° C. per minute and calcined at this temperature for 4 hours. A 9.83 g sample of the calcined material was suspended in a solution of 0.538 g of $KNO_3$ in 17 mL of deionized water stirred for 30 minutes and rotovaped dry at 60° C. followed by calcination for 2 hours at 110° C. The nominal composition of the catalyst: 54.3 wt. % Ag and 5.2 wt. % $KNO_3$.

F. Run 6: To 11.25 g of deionized water 11.01 g of ethylenediamine was added followed by slow addition of 11.08 g oxalic acid dihydrate at 50° C. To the resulting homogeneous solution 20.30 g of silver oxide and 4.0 g of ethanolamine at 50° C. and stirred until dissolved. ⅓ portion of the resulting solution was combined with 4.67 g of basic gamma-$Al_2O_3$ (SigmaAldrich) and mixed well into a homogeneous thick paste, which was placed in an oven at 110°C for 1 hour then heated to 300° C. at the rate of 20° C. per minute and calcined at this temperature for 4 hours. A 9.78 g sample of the calcined material was suspended in a solution of 0.517 g of $KNO_3$ in 17 mL of deionized water stirred for 30 minutes and rotovaped dry at 60° C. followed by calcination for 2 hours at 110° C. The nominal composition of the catalyst: 54.3 wt. % Ag and 5.3 wt. % $KNO_3$.

G. Run 7: To 11.0 g of deionized water 11.07 g of ethylenediamine was added followed by slow addition of 11.11 g oxalic acid dihydrate at 50° C. To the resulting homogeneous solution 20.52 g of silver oxide and 4.0 g of ethanolamine at 50° C. and stirred until dissolved. ¼ portion of the resulting solution was combined with 3.49 g of silica support (PQ grade 3050) and mixed well into a homogeneous thick paste, which was placed in an oven at 110° C. for 1 hour then heated to 300° C. at the rate of 20° C. per minute and calcined at this temperature for 4 hours. A 7.58 g sample of the calcined material was suspended in a solution of 0.415 g of $KNO_3$ in 17 mL of deionized water stirred for 30 minutes and rotovaped dry at 60° C. followed by calcination for 2 hours at 110° C. The nominal composition of the catalyst: 54.8 wt. % Ag and 5.2 wt. % $KNO_3$.

H. Run 8: To 11.03 mL of deionized water 11.05 g of ethylenediamine was added followed by slow addition of 11.08 g oxalic acid dihydrate at 50° C. To the resulting homogeneous solution 20.30 g of silver oxide and 4.0 g of ethanolamine at 50° C. and stirred until dissolved. ⅓ portion of the resulting solution was combined with 4.6 g of mesoporous silica MCM-41 (Sigma Aldrich) and mixed well into a homogeneous thick paste, which was placed in an oven at 110° C. for 1 hour then heated to 300° C. at the rate of 20° C. per minute and calcined at this temperature for 4 hours. A 9.61 g sample of the calcined material was suspended in a solution of 0.517 g of $KNO_3$ in 17 mL of deionized water stirred for 30 minutes and rotovaped dry at 60° C. followed by calcination for 2 hours at 110° C. The nominal composition of the catalyst: 54.3 wt. % Ag and 5.1 wt. % $KNO_3$.

I. Run 9: To 11.03 mL of deionized water 11.05 g of ethylenediamine was added followed by slow addition of 11.08 g oxalic acid dihydrate at 50° C. To the resulting homogeneous solution 20.30 g of silver oxide and 4.0 g of ethanolamine at 50° C. and stirred until dissolved. ⅓ portion of the resulting solution was combined with 4.56 g of Florisil® ($MgSiO_3$) support (Sigma Aldrich) and mixed well into a homogeneous thick paste, which was placed in an oven at 110° C. for 1 hour then heated to 300° C. at the rate of 20° C. per minute and calcined at this temperature for 4 hours. A 9.90 g sample of the calcined material was suspended in a solution of 0.557 g of $KNO_3$ in 17 ml of deionized water stirred for 30 minutes and rotovaped dry at 60° C. followed by calcination for 2 hours at 110° C. The nominal composition of the catalyst: 54.9 wt. % Ag and 5.3 wt. % $KNO_3$.

J. Run 10: To 11.25 g of deionized water 11.01 g of ethylenediamine was added followed by slow addition of 11.08 g oxalic acid dihydrate at 50° C. To the resulting homogeneous solution 20.33 g of silver oxide and 4.0 g of ethanolamine at 50° C. and stirred until dissolved. ⅓ portion of the resulting solution was combined with 4.51 g of MgO (SigmaAldrich) and mixed well into a homogeneous thick paste, which was placed in an oven at 110° C. for 1 hour then heated to 300° C. at the rate of 20° C. per minute and calcined at this temperature for 4 hours. A 10.08 g sample of the calcined material was suspended in a solution of 0.56 g of $KNO_3$ in 17 mL of deionized water stirred for 30 minutes and rotovaped dry at 60° C. followed by calcination for 2 hours at 110° C. The nominal composition of the catalyst: 55.1 wt. % Ag and 5.3 wt. % $KNO_3$.

K. Run 11: To 11.4 g of deionized water 11.05 g of ethylenediamine was added followed by slow addition of 11.05 g oxalic acid dihydrate at 50° C. To the resulting homogeneous solution 20.51 g of silver oxide and 4.0 g of ethanolamine at 50° C. and stirred until dissolved. ⅓ portion of the resulting solution was combined with 4.64 g of zirconium hydroxide (Sigma Aldrich) and mixed well into a homogeneous thick paste, which was placed in an oven at 110° C. for 1 hour then heated to 300° C. at the rate of 20° C. per minute and calcined at this temperature for 4 hours. A 8.58 g sample of the calcined material was suspended in a solution of 0.516 g of $KNO_3$ in 17 mL of deionized water stirred for 30 minutes and rotovaped dry at 60° C. followed by calcination for 2 hours at 110° C. The nominal composition of the catalyst: 55.2 wt. % Ag and 5.7 wt. % $KNO_3$.

L. Run 12: To 11.4 g of deionized water 11.05 g of ethylenediamine was added followed by slow addition of 11.05 g oxalic acid dihydrate at 50° C. To the resulting homogeneous solution 20.51 g of silver oxide and 4.0 g of ethanolamine at 50° C. and stirred until dissolved. ⅓ portion of the resulting solution was combined with 4.78 g of hydroxyapatite (Sigma Aldrich) and mixed well into a homogeneous thick paste, which was placed in an oven at 110° C. for 1 hour then heated to 300° C. at the rate of 20° C. per minute and calcined at this temperature for 4 hours. A 9.62 g sample of the calcined material was suspended in a solution of 0.546 g of $KNO_3$ in 17 mL of deionized water stirred for 30 minutes and rotovaped dry at 60° C. followed by calcination for 2 hours at 110° C. The nominal composition of the catalyst: 55.4 wt. % Ag and 5.4 wt. % $KNO_3$.

M. Run 13: To 11.4 g of deionized water 11.05 g of ethylenediamine was added followed by slow addition of 11.05 g oxalic acid dihydrate at 50° C. To the resulting homogeneous solution 20.51 g of silver oxide and 4.0 g of ethanolamine at 50° C. and stirred until dissolved. ⅓ portion of the resulting solution was combined with 4.59 g of synthetic hydrotalcite (Sigma Aldrich) and mixed well into a homogeneous thick paste, which was placed in an oven at 110° C. for 1 hour then heated to 300° C. at the rate of 20° C. per minute and calcined at this temperature for 4 hours. A 8.73 g sample of the calcined material was suspended in a solution of 0.511 g of $KNO_3$ in 17 mL of deionized water stirred for 30 minutes and rotovaped dry at 60° C. followed by calcination for 2 hours at 110° C. The nominal composition of the catalyst: 55.2 wt. % Ag and 5.0 wt. % $KNO_3$.

N. Run 14: To 11.05 g of deionized water 11.22 g of ethylenediamine was added followed by slow addition of 11.20 g oxalic acid dihydrate at 50° C. To the resulting homogeneous solution 20.42 g of silver oxide and 4.0 g of ethanolamine at 50° C. and stirred until dissolved. Half of the resulting solution was combined with 11.55 g of talc (Sigma Aldrich) and mixed well into a homogeneous thick paste, which was placed in an oven at 110° C. for 1 hour then heated to 300° C. at the rate of 20° C. per minute and calcined at this temperature for 4 hours. A 4.0 g sample of the calcined material was suspended in a solution of 0.203 g of $KNO_3$ in 9 mL of deionized water stirred for 30 minutes and rotovaped dry at 60° C. followed by calcination for 2 hours at 110° C. The nominal composition of the catalyst: 43.0 wt. % Ag and 4.8 wt. % $KNO_3$.

O. Run 15: To 11.82 g of deionized water 11.46 g of ethylenediamine was added followed by slow addition of 11.52 g oxalic acid dihydrate at 50° C. To the resulting homogeneous solution 20.93 g of silver oxide and 4.0 g of ethanolamine at 50° C. and stirred until dissolved. A ⅓ portion of the resulting solution was combined with 4.51 g of talc (Sigma Aldrich), calcined 6 hours at 300° C., and mixed well into a homogeneous thick paste, which was placed in an oven at 110° C. for 1 hour then heated to 300° C. at the rate of 20° C. per minute and calcined at this temperature for 4 hours. A 9.33 g sample of the calcined material was suspended in a solution of 0.525 g of $KNO_3$ in 17 mL of deionized water stirred for 30 minutes and rotovaped dry at 60° C. followed by calcination for 2 hours at 110° C. The nominal composition of the catalyst: 55.9 wt. % Ag and 5.3 wt. % $KNO_3$.

P. Run 16: To 11.82 g of deionized water 11.46 g of ethylenediamine was added followed by slow addition of 11.52 g oxalic acid dihydrate at 50° C. To the resulting homogeneous solution 20.93 g of silver oxide and 4.0 g of ethanolamine at 50° C. and stirred until dissolved. A ⅓ portion of the resulting solution was combined with 4.54 g of talc (Sigma Aldrich), calcined 6 hours at 600° C., and mixed well into a homogeneous thick paste, which was placed in an oven at 110° C. for 1 hour then heated to 300° C. at the rate of 20° C. per minute and calcined at this temperature for 4 hours. A 9.3 g sample of the calcined material was suspended in a solution of 0.51 g of $KNO_3$ in 17 mL of deionized water stirred for 30 minutes and rotovaped dry at 60° C. followed by calcination for 2 hours at 110° C. The nominal composition of the catalyst: 55.9 wt. % Ag and 5.2 wt. % $KNO_3$.

Q. Run 17: To 11.2 mL of deionized water 11.05 g of ethylenediamine was added followed by slow addition of 11.11 g oxalic acid dihydrate at 50° C. To the resulting homogeneous solution 20.4 g of silver oxide and 4.0 g of ethanolamine at 50° C. and stirred until dissolved followed by addition of 0.270 g of $NH_4ReO_4$. ⅓ of the resulting solution was combined with 4.78 g of talc (Sigma Aldrich) and mixed well into a homogeneous thick paste, which was placed in an oven at 110° C. for 1 hour then heated to 300° C. at the rate of 20° C. per minute and calcined at this temperature for 4 hours. A 9.63 g sample of the calcined material was suspended in a solution of 0.532 g of $KNO_3$ in 17 mL of deionized water stirred for 30 minutes and rotovaped dry at 60° C. followed by calcination for 2 hours at 110° C. The nominal composition of the catalyst: 53.6 wt. % Ag, 0.56 wt. % Re and 5.2 wt % $KNO_3$.

R. Run 18: To 11.43 mL of deionized water 11.21 g of ethylenediamine was added followed by slow addition of 11.15 g oxalic acid dihydrate at 50° C. To the resulting homogeneous solution 20.1 g of silver oxide and 4.0 g of ethanolamine at 50° C. and stirred until dissolved, followed by addition of 0.564 g of $(NH_4)_6Mo_7O_{24}$ tetrahydrate. ⅓ of the resulting solution was combined with 4.85 g of talc (Sigma Aldrich) and mixed well into a homogeneous thick paste, which was placed in an oven at 110° C. for 1 hour then heated to 300° C. at the rate of 20° C. per minute and calcined at this temperature for 4 hours. A 9.98 g sample of the calcined material was suspended in a solution of 0.549 g of $KNO_3$ in 17 mL of deionized water stirred for 30 minutes and rotovaped dry at 60° C. followed by calcination for 2 hours at 110° C. The nominal composition of the catalyst: 52.4 wt. % Ag, 0.96 wt. % Mo and 5.2 wt. % $KNO_3$.

S. Run 19: To 11.05 g of deionized water 11.22 g of ethylenediamine was added followed by slow addition of 11.20 g oxalic acid dihydrate at 50° C. To the resulting homogeneous solution 20.42 g of silver oxide and 4.0 g of ethanolamine at 50° C. and stirred until dissolved. Half of the resulting solution was combined with 11.08 g of kaolinite (Sigma Aldrich) and mixed well into a homogeneous thick paste, which was placed in an oven at 110° C. for 1 hour then heated to 300° C. at the rate of 20° C. per minute and calcined at this temperature for 4 hours. A 4.03 g sample of the calcined material was suspended in a solution of 0.208 g of $KNO_3$ in 9 mL of deionized water stirred for 30 minutes and rotovaped dry at 60° C. followed by calcination for 2 hours at 110° C. The nominal composition of the catalyst: 43.9 wt. % Ag and 4.9 wt. % $KNO_3$.

T. Run 20: To 11.9 g of deionized water 11.20 g of ethylenediamine was added followed by slow addition of 11.14 g oxalic acid dihydrate at 50° C. To the resulting homogeneous solution 20.6 g of silver oxide and 4.0 g of ethanolamine at 50° C. and stirred until dissolved. A ⅓ portion of the resulting solution was combined with 4.63 g of kaolinite (Sigma Aldrich), calcined 6 hours at 300° C., and mixed well into a homogeneous thick paste, which was placed in an oven at 110° C. for 1 hour then heated to 300° C. at the rate of 20° C. per minute and calcined at this temperature for 4 hours. A 9.0 g sample of the calcined material was suspended in a solution of 0.505 g of $KNO_3$ in 17 mL of deionized water stirred for 30 minutes and rotovaped dry at 60° C. followed by calcination for 2 hours at 110° C. The nominal composition of the catalyst: 54.9 wt. % Ag and 5.3 wt. % $KNO_3$.

U. Run 21: To 11.9 g of deionized water 11.20 g of ethylenediamine was added followed by slow addition of 11.14 g oxalic acid dihydrate at 50° C. To the resulting homogeneous solution 20.6 g of silver oxide and 4.0 g of ethanolamine at 50° C. and stirred until dissolved. A ⅓ portion of the resulting solution was combined with 4.57 g of kaolinite (Sigma Aldrich), calcined 6 hours at 600° C., and mixed well into a homogeneous thick paste, which was placed in an oven at 110° C. for 1 hour then heated to 300° C. at the rate of 20° C. per minute and calcined at this temperature for 4 hours. A 9.53 g sample of the calcined material was suspended in a solution of 0.54 g of $KNO_3$ in 17 mL of deionized water stirred for 30 minutes and rotovaped dry at 60° C. followed by calcination for 2 hours at 110° C. The nominal composition of the catalyst: 55.0 wt. % Ag and 5.7 wt. % $KNO_3$.

V. Run 22: To 11.9 g of deionized water 11.20 g of ethylenediamine was added followed by slow addition of 11.14 g oxalic acid dihydrate at 50° C. To the resulting homogeneous solution 20.6 g of silver oxide and 4.0 g of ethanolamine at 50° C. and stirred until dissolved. A ⅓ portion of the resulting solution was combined with 4.59 g of kaolinite (Sigma Aldrich), calcined 6 hours at 800° C., and mixed well into a homogeneous thick paste, which was placed in an oven at 110° C. for 1 hour then heated to 300° C. at the rate of 20° C. per minute and calcined at this temperature for 4 hours. A 8.75 g sample of the calcined material was suspended in a solution of 0.486 g of $KNO_3$ in 17 mL of deionized water stirred for 30 minutes and rotovaped dry at 60° C. followed by calcination for 2 hours at 110° C. The nominal composition of the catalyst: 55.1 wt. % Ag and 5.3 wt. % $KNO_3$.

W. Run 23: To 11.2 mL of deionized water 11.05 g of ethylenediamine was added followed by slow addition of 11.11 g oxalic acid dihydrate at 50° C. To the resulting homogeneous solution 20.4 g of silver oxide and 4.0 g of ethanolamine at 50° C. and stirred until dissolved followed by addition of 0.270 g of $NH_4ReO_4$. ⅓ of the resulting solution was combined with 4.85 g of kaolinite (Sigma Aldrich) and mixed well into a homogeneous thick paste, which was placed in an oven at 110° C. for 1 hour then heated to 300° C. at the rate of 20° C. per minute and calcined at this temperature for 4 hours. A 9.82 g sample of the calcined material was suspended in a solution of 0.541 g of $KNO_3$ in 17 mL of deionized water stirred for 30 minutes and rotovaped dry at 60° C. followed by calcination for 2 hours at 110° C. The nominal composition of the catalyst: 53.2 wt. % Ag, 0.55 wt. % Re and 5.2 wt. % $KNO_3$.

X. Run 24: To 11.43 mL of deionized water 11.21 g of ethylenediamine was added followed by slow addition of 11.15 g oxalic acid dihydrate at 50° C. To the resulting homogeneous solution 20.1 g of silver oxide and 4.0 g of ethanolamine at 50° C. and stirred until dissolved, followed by addition of 0.564 g of $(NH_4)_6Mo_7O_{24}$ tetrahydrate. ⅓ of the resulting solution was combined with 4.75 g of kaolinite (Sigma Aldrich) and mixed well into a homogeneous thick paste, which was placed in an oven at 110° C. for 1 hour then heated to 300° C. at the rate of 20° C. per minute and calcined at this temperature for 4 hours. A 10.32 g sample of the calcined material was suspended in a solution of 0.576 g of $KNO_3$ in 17 mL of deionized water stirred for 30 minutes and rotovaped dry at 60° C. followed by calcination for 2 hours at 110° C. The nominal composition of the catalyst: 52.9 wt. % Ag, 0.97 wt. % Mo and 5.3 wt. % $KNO_3$.

Y. Run 25: To 11.0 g of deionized water 11.105 g of ethylenediamine was added followed by slow addition of 11.07 g oxalic acid dihydrate at 50° C. To the resulting homogeneous solution 20.14 g of silver oxide and 4.0 g of ethanolamine at 50° C. and stirred until dissolved. A ⅐ aliquote of the resulting solution was combined with 4.05 g of pyrophilite (ProFylite® product of U.S. Aragonite Co.) and mixed well into a homogeneous thick paste, which was placed in an oven at 110° C. for 1 hour then heated to 300° C. at the rate of 20° C. per minute and calcined at this temperature for 4 hours. A 5.65 g sample of the calcined material was suspended in a solution of 0.278 g of $KNO_3$ in 9 mL of deionized water stirred for 30 minutes and rotovaped dry at 60° C. followed by calcination for 2 hours at 110° C. The nominal composition of the catalyst: 38 wt. % Ag and 4.5 wt. % $KNO_3$.

Z. Run 26: To 11.2 mL of deionized water 11.05 g of ethylenediamine was added followed by slow addition of 11.11 g oxalic acid dihydrate at 50° C. To the resulting homogeneous solution 20.4 g of silver oxide and 4.0 g of ethanolamine at 50° C. and stirred until dissolved followed by addition of 0.270 g of $NH_4ReO_4$. ⅓ of the resulting solution was combined with 4.62 g of pyrophilite (ProFylite® product of U.S. Aragonite Co.) and mixed well into a homogeneous thick paste, which was placed in an oven at 110° C. for 1 hour then heated to 300° C. at the rate of 20° C. per minute and calcined at this temperature for 4 hours. A 10.1 g sample of the calcined material was suspended in a solution of 0.553 g of $KNO_3$ in 17 mL of deionized water stirred for 30 minutes and rotovaped dry at 60° C. followed by calcination for 2 hours at 110° C. The nominal composition of the catalyst: 54.4 wt. % Ag, 0.57 wt. % Re and 5.2 wt. % $KNO_3$.

AA. Run 27: To 11.43 mL of deionized water 11.21 g of ethylenediamine was added followed by slow addition of 11.15 g oxalic acid dihydrate at 50° C. To the resulting homogeneous solution 20.1 g of silver oxide and 4.0 g of ethanolamine at 50° C. and stirred until dissolved, followed by addition of 0.564 g of $(NH_4)_6Mo_7O_{24}$ tetrahydrate. ⅓ of the resulting solution was combined with 4.87 g pyrophillite (ProFylite® product of U.S. Aragonite Co.) and mixed well into a homogeneous thick paste, which was placed in an oven at 110° C. for 1 hour then heated to 300° C. at the rate of 20° C. per minute and calcined at this temperature for 4 hours. A 10.33 g sample of the calcined material was suspended in a solution of 0.571 g of $KNO_3$ in 17 mL of deionized water stirred for 30 minutes and rotovaped dry at 60° C. followed by calcination for 2 hours at 110° C. The nominal composition of the catalyst: 52.4 wt. % Ag, 0.97 wt. % Mo and 5.4 wt. % $KNO_3$.

Example 2

Catalyst Testing

The catalysts were tested in a ⅜ in (6.35 mm) stainless steel fixed bed reactor using 2 g of catalyst diluted with 2 g of silicon carbide powder. A continuous flow of 6.0 mol % of propylene and 7.0 mol % of oxygen diluted by nitrogen was applied at 1200 $h^{-1}$ space flow velocity to the catalyst in the presence of 180 ppm of EtCl and 70 ppm of NO feed modifiers. The catalyst performance was determined at 2 barg (200 kPa) pressure and 255° C. after reaching a steady performance. The results are presented in Table 1. Propylene oxide selectivity is calculated by the formula 100*[PO made]/([PO made]+[$CO_2$ made]/3). Propylene conversion is calculated by the formula 100*([PO made]+[$CO_2$ made]/3)/([PO made]+[$CO_2$ made]/3+[Propylene unreacted]). $O_2$ (oxygen) conversion is calculated by the formula 100*([PO made]/2+[$CO_2$ made])/([PO made]/2+[$CO_2$ made]+[$O_2$ unreacted]).

TABLE 1

Results of Epoxidation Based Upon Catalyst Composition at 255° C.

| Run | Catalyst System | Propylene Oxide Selectivity (%) | Propylene Conversion (%) | $O_2$ conversion (%) |
|---|---|---|---|---|
| 1 | Ag/$CaCO_3$/$KNO_3$ | 51.60 | 20.60 | 53.40 |
| 2 | Ag/Mo/$CaCO_3$/$KNO_3$ | 48.60 | 14.70 | 29.80 |
| 3 | Ag/Re/$CaCO_3$/$KNO_3$ | 45.50 | 16.20 | 35.50 |
| 4 | Ag/Ca(OH)$_2$/$KNO_3$ | 49.00 | 8.35 | 15.99 |
| 5 | Ag/alpha-$Al_2O_3$/$KNO_3$ | 26.30 | 7.60 | 20.40 |
| 6 | Ag/basic gamma-$Al_2O_3$/$KNO_3$ | 0.00 | 18.81 | 98.95 |
| 7 | Ag/$SiO_2$/$KNO_3$ | 0.00 | 5.60 | 18.50 |
| 8 | Ag/MCM-41-Hex $SiO_2$/$KNO_3$ | 0.00 | 8.20 | 29.20 |
| 9 | Ag/Florisil ®($MgSiO_3$)/$KNO_3$ | 0.60 | 19.53 | 94.70 |
| 10 | Ag/MgO/$KNO_3$ | 2.80 | 13.10 | 49.10 |
| 11 | Ag/Zr(OH)$_4$ | 1.04 | 15.53 | 64.50 |
| 12 | Ag/hydroxyapatite | 28.90 | 2.81 | 6.88 |
| 13 | Ag/hydrotalcite | 0.49 | 8.05 | 27.16 |
| 14 | Ag/talc/$KNO_3$ | 47.30 | 15.40 | 42.00 |
| 15 | Ag/talc-300° C./$KNO_3$ | 42.30 | 11.80 | 24.90 |
| 16 | Ag/talc-600° C./$KNO_3$ | 40.40 | 15.00 | 40.40 |
| 17 | Ag/Re/talc/$KNO_3$ | 42.00 | 18.40 | 43.20 |
| 18 | Ag/Mo/talc/$KNO_3$ | 5.90 | 0.67 | 1.90 |
| 19 | Ag/kaolinite/$KNO_3$ | 54.50 | 8.60 | 18.90 |
| 20 | Ag/kaolinite-300° C./$KNO_3$ | 54.40 | 9.60 | 21.20 |
| 21 | Ag/kaolinite-600° C./$KNO_3$[a] | 44.70 | 1.70 | 4.00 |
| 22 | Ag/kaolinite-800° C./$KNO_3$[a] | 22.90 | 0.60 | 1.80 |
| 23 | Ag/Re/kaolinite/$KNO_3$ | 49.00 | 12.50 | 24.30 |
| 24 | Ag/Mo/kaolinite/$KNO_3$ | 2.20 | 0.26 | 0.84 |
| 25 | Ag/pyrophyllite/$KNO_3$ | 37.30 | 4.90 | 10.80 |
| 26 | Ag/Re/pyrophillite/$KNO_3$ | 32.60 | 10.70 | 30.30 |
| 27 | Ag/Mo/pyrophyllite/$KNO_3$ | 0.00 | 0.16 | 0.57 |

[a]testing temperature is 265° C.

Calcination of the kaolinite support over 600° C., when it transforms into metakaoline (amorphous $Al_2Si_2O_7$) with loss of layered structure, results in performance loss as can be seen in Table 1. Talc, on the other hand, retains structure and performance even if the support is calcined at 600° C. before catalyst synthesis. Compositionally similar to talc, amorphous Florisil® support ($MgSiO_3$) did not produce propylene oxide under the experimental conditions and produced $CO_2$ at high conversion of the feed. Without wishing to be bound by any theory, it is believed that the crystallinity of the support is a useful parameter for obtaining good performance. Re modification of the talc/kaolinite/pyrophillite based silver catalysts showed improvement in activity, while Mo modification resulted in complete loss of activity.

Example 3

Reduced Metal Loading

A variety of epoxidation catalysts were tested in a ⅜ in (6.35 mm) stainless steel fixed bed reactor using 2 g of catalyst. A continuous flow of 7.6 mol % of propylene and 7.0 mol % of oxygen diluted by nitrogen was applied at 1200 $h^{-1}$ space flow velocity to the catalyst in the presence of 200 ppm of EtCl and 75 ppm of NO feed modifiers. The catalyst performance was determined at 2 barg (200 kPa) pressure and 255° C. after reaching a steady performance after 24 hours. The results are presented in Table 2.

Comparative catalyst 1 was formed via the process described regarding Run 1 of Example 1, with the concentrations listed in Table 2. Comparative catalysts 2, 3, 4 and inventive catalyst 1 and 2 were prepared using Kaolinite support commercially available from Sigma Aldrich Co. via the process described regarding Run 19 of Example 1, with the concentrations listed in Table 2.

TABLE 2

| Example | Support | Ag Content (wt. %) | K Content (wt. %) | Propylene Conversion | PO Selectivity | PO Productivity lb/gf/hr |
|---|---|---|---|---|---|---|
| Comp 1 | $CaCO_3$ | 56.5 | 2.3 | 16.6 | 41.2 | 1.0 |
| Comp 2 | Kaolinite | 56.4 | 2.3 | 7.9 | 49.7 | 0.6 |
| Comp 3 | Kaolinite | 47.5 | 1.2 | 12.2 | 16.0 | 0.3 |
| Inv 1 | Kaolinite | 46.9 | 2.3 | 10.1 | 54.2 | 0.9 |
| Inv 2 | Kaolinite | 46.5 | 3.3 | 9.0 | 53.0 | 0.8 |
| Comp 4 | Kaolinite | 46.0 | 4.4 | 8.9 | 45.6 | 0.6 |

It was observed that the inventive catalyst 1 and 2 exhibited increased conversion, selectivity and productivity over the comparative examples at the same promoter (K content) concentration. However, it was further observed that increasing the promoter concentration did not necessarily increase performance.

While the foregoing is directed to embodiments as disclosed herein, other and further embodiments may be devised without departing from the basic scope thereof and the scope thereof is determined by the claims that follow.

What is claimed is:

1. A method comprising:
   carrying out selective oxidation, in the vapor phase, of an olefinic compound with molecular oxygen to produce an epoxide, wherein the selective oxidation is carried out in the presence of an epoxidation catalyst, and wherein the epoxidation catalyst comprises: (i) more than 5 wt. % to 80 wt. % of a metal component and (ii) a support comprising a phyllosilicate,
   wherein the olefinic compound and the epoxidation catalyst are introduced to a reaction vessel via an input stream prior to introducing the molecular oxygen to the reaction vessel.

2. The method of claim 1, wherein the phyllosilicate is kaolinite.

3. The method of claim 1, wherein the phyllosilicate has the chemical formula: $Mg_3Si_2O_5(OH)_4$.

4. The method of claim 1, wherein the phyllosilicate has the chemical formula: $X_2Y_4\text{-}6Z_8O_{10}(OH,F)_4$, wherein the X is selected from: K, Na, Ca, or other Group I or Group II metals; Y is selected from: Al, Mg, and Fe; Z is selected from Si, A, $Fe^{3+}$, and Ti.

5. The method of claim 1, wherein the support comprises one or more components selected from the group consisting of: metal oxides and alkaline earth carbonates.

6. The method of claim 3, wherein the metal oxide is selected from the group consisting of: alumina, silica titania, zirconia, and mixtures thereof.

7. The method of claim 1, wherein the metal component is silver.

8. The method of claim 1, wherein the olefinic compound is selected from the group consisting of: ethylene, propylene, butene, and combinations thereof.

9. The method of claim 1, wherein the metal component is present in the range of 5 wt. % to 50 wt. % based on the total weight of the epoxidation catalyst.

10. The method of claim 1, wherein epoxidation catalyst further comprises a Group I metal salt.

11. The method of claim 10, wherein Group I metal salt is selected from the group consisting of: lithium nitrate, sodium nitrate, potassium nitrate, or combinations thereof.

12. The method of claim 10, wherein the Group I metal salt is present in the range of 0.01 wt. % to 10 wt. % based on the total weight of the epoxidation catalyst.

13. The method of claim 1, wherein the epoxidation catalyst additionally comprises a promoter selected from the group consisting of: rhenium, molybdenum, tungsten, iron, nickel, copper, zinc, scandium, ytterbium, or combinations thereof, and wherein the promoter is present in the range of from 0.01 wt. % to 10 wt. % based on the total weight of the epoxidation catalyst.

14. The method of claim 1, wherein the olefinic compound is introduced into an epoxidation reactor where the selective oxidation is carried out in an amount in the range of 0.1 vol. % to 50 vol. % based on a total volume of reaction mixture.

15. The method of claim 1, wherein the olefinic compound and molecular oxygen are reacted at a temperature in the range of 100° C. to 500° C. and a pressure in the range of 1 barg to 30 barg.

16. The method of claim 1, wherein the molecular oxygen is introduced into an epoxidation reactor wherein the selective oxidation is carried out in an amount in the range of 1 vol. % to 11 vol. % based on a total volume of reaction mixture.

* * * * *